United States Patent [19]

Matsumoto et al.

[11] 4,238,419
[45] Dec. 9, 1980

[54] HYDROFORMYLATION OF OLEFINIC COMPOUNDS

[75] Inventors: Mitsuo Matsumoto; Masuhiko Tamura, both of Kurashiki, Japan

[73] Assignee: Kuraray Co., Ltd., Kurashiki, Japan

[21] Appl. No.: 45,301

[22] Filed: Jun. 4, 1979

[30] Foreign Application Priority Data

Jun. 5, 1978 [JP] Japan .............................. 53-68085
Sep. 26, 1978 [JP] Japan .............................. 53-118908
Sep. 26, 1978 [JP] Japan .............................. 53-118909

[51] Int. Cl.$^3$ ............................................ C07C 45/50
[52] U.S. Cl. .............................. 568/454; 252/431 R; 252/431 P
[58] Field of Search ............... 260/604 HF, 345.9; 568/909, 882; 560/207

[56] References Cited

U.S. PATENT DOCUMENTS

| | | | |
|---|---|---|---|
| 3,954,877 | 5/1976 | Gipson | 260/604 HF |
| 4,060,557 | 11/1977 | Macaluso et al. | 260/604 HF |
| 4,101,588 | 7/1978 | Nieuburg et al. | 260/604 HF |
| 4,142,992 | 3/1979 | Knowles et al. | 252/431 P |

OTHER PUBLICATIONS

Miller, Clay Robert et al., *Journal of the American Chemical Society* vol. 79, (1957) pp. 424–427.
Grayson, M. et al., *Tetrahedron*, vol. 23, (1967) pp. 1065–1078.
Bird, C. W., *Chemical Reviews*, vol. 62, (1962) pp. 289–291.

*Primary Examiner*—Natalie Trousof
*Assistant Examiner*—L. Hendriksen
*Attorney, Agent, or Firm*—Barry Kramer

[57] ABSTRACT

Rhodium catalyzed hydroformylation of olefinic compounds is essentially effected in the presence of a secondary phosphine oxide of the general formula (I) in an amount of at least one mole per gram atom of rhodium, which supresses the thermal degradation of the rhodium catalyst in the hydroformylation stage as well as in the distillation of the reaction products:

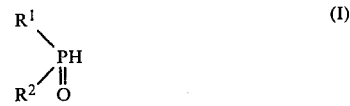

(I)

wherein, in the formula (I), $R^1$ and $R^2$ are the same or different, substituted or unsubstituted hydrocarbon residues containing not more than 20 carbon atoms.

The phosphine oxide of the general formula (I) maintains the catalytic activity over a prolonged period of time and prevents essentially metallic rhodium from sticking to the vessel during distillation of the reaction products from the reaction mixture, and consequently makes recycle of the catalyst easier and enables lowering the hydroformylation pressure.

15 Claims, No Drawings

HYDROFORMYLATION OF OLEFINIC COMPOUNDS

BACKGROUND OF THE INVENTION

1. Field of the Invention

This invention relates to a process for the hydroformylation of olefinic compounds.

2. Description of the Prior Art

One known hydroformylation reaction comprises reacting olefins with a mixed hydrogen/carbon monoxide gas in an organic solvent in the presence of a rhodium catalyst to produce aldehydes with one more carbon atom. This reaction has found industrial use in the production of butyraldehydes from propylene and propionaldehyde from ethylene, for instance. In commercially practicing this hydroformylation reaction, the most serious problem is maintaining the life of the rhodium catalyst because the rhodium catalyst is very expensive.

A number of research investigations have been made for maintaining the catalytic activity of rhodium catalyst in the hydroformylation of olefins. Heretofore, it has been assumed that thermal degradation of the rhodium catalyst is one of the main causes of the activity decrease. Therefore, in order to maintain the catalytic activity, it was necessary to conduct the hydroformylation of ethylene or propylene under very strictly controlled reaction conditions, especially at an adequate reaction temperature and under well selected reaction pressure.

The maintenance of the catalytic activity by the strict adjustment of the reaction conditions is practically applicable only to the hydroformylation of lower boiling olefins such as ethylene and propylene where the reaction products have relatively lower boiling points. In the hydroformylation of these olefins, higher temperature is not required because of ease of distilling off the reaction products from the reaction mixture. On the other hand, in the hydroformylation of olefins where the reaction products are higher boiling aldehydes (e.g. olefins having 5 or more carbon atoms and substituted olefins) it is generally desirable from an industrial viewpoint that the reaction products be separated from the reaction mixture by distillation. During the distillation, however, a part of the rhodium catalyst tends to thermally decompose in the distillation vessel and the resulting metallic rhodium adheres to local portions of the vessel wall. Such metallic rhodium formation not only makes recycling or reuse of the catalyst difficult, but it also necessitates regeneration under severe reaction conditions (high temperature and pressure). For these reasons, the rhodium catalyzed hydroformylation of such olefins under mild reaction conditions has never been practiced commercially.

SUMMARY OF THE INVENTION

It has now been found that the above problems can be solved according to the present invention in a very simple manner by adding to the reaction system for hydroformylation of olefinic compounds, a secondary phosphine oxide having the general formula (I)

in an amount of at least one mole per gram atom of rhodium, wherein, in formula (I), $R^1$ and $R^2$ are the same or different, substituted or unsubstituted hydrocarbon residues having not more than about 20 carbon atoms.

The use of the above secondary phosphine oxides according to the invention suppresses the thermal degradation of the catalyst, and, as a result, maintains the catalytic activity for a long period of time even when relatively high reaction temperatures are employed. Further, even when the reaction mixture containing the catalyst is heated to separate the unreacted starting material and the products by distillation, sticking of metallic rhodium to the vessel wall is substantially prevented. Moreover, when the catalyst components in the distillation residue are recycled to the hydroformylation system, the catalytic activity is satisfactorily maintained under the same reaction conditions without any treatment of the residue. Thus, according to the invention, not only is the stability of the catalytic activity in the hydroformylation process increased, but also the deactivation of the catalyst due to thermal decomposition during the separation of the products is prevented and the recycling of the catalyst can be realized with great advantage.

According to this invention, olefinic compounds affording higher boiling aldehydes, as well as lower boiling aldehydes, as a main product can thus be hydroformylated industrially. In the hydroformylation of ethylene or propylene, the present invention has an effect on the maintenance of the catalyst life at relatively high temperatures at which the products can be separated from the reaction mixture effectively and at which high reaction rates can be achieved. Thus, the present invention has a very great commercial importance.

DETAILED DESCRIPTION OF THE INVENTION

In general formula (I), $R^1$ and $R^2$ are the same or different and each is a substituted or an unsubstituted hydrocarbon residue having not more than about 20 carbon atoms, such as a saturated aliphatic hydrocarbon residue (e.g. methyl, ethyl, propyl, butyl, pentyl, hexyl, heptyl, octyl, nonyl, decyl, dodecyl), an aromatic hydrocarbon residue (e.g. phenyl, tolyl, ethylphenyl, xylyl) or an alicyclic hydrocarbon residue (e.g. cyclohexyl, methylcyclohexyl). The substituent in the substituted hydrocarbon residue can include a heteroatom or a group containing one or more heteroatoms, such as fluorine atom, lower alkoxy, hydroxyl or amino, provided that it should not be a poison to the rhodium catalyst and should not cause unfavorable side reactions.

Examples of a secondary phosphine oxide represented by general formula (I) are as follows (here and elsewhere in this disclosure Ph means phenyl):

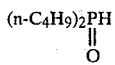 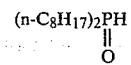 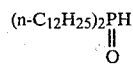

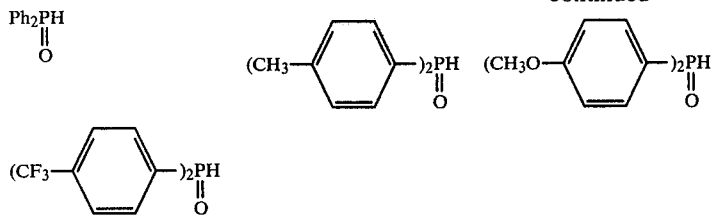

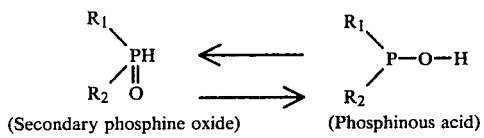

The state in which the secondary phosphine oxide exists in the reaction system is not clear, but, according to Tetrahedron, 23, 1065 (1967), it is known that the secondary phosphine oxide is in a tautomeric relation with the corresponding phosphinous acid and the keto form (the left side in the equation shown below) is preferential in the equilibrium state according to the equation:

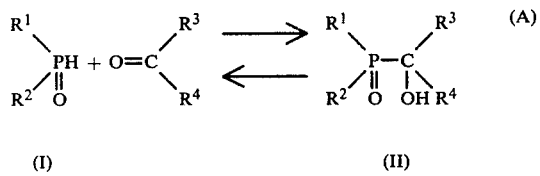

(Secondary phosphine oxide)   (Phosphinous acid)

It is also known that the secondary phosphine oxide of general formula (I), when brought into contact with an aldehyde or ketone, gives, according to the equation (A) shown below, organophosphorus compounds represented by the general formula (II) (cf. e.g. J. Amer. Chem. Soc., 79, 424 (1957)):

$$\begin{array}{c} R^1 \\ \phantom{R}\diagdown \\ \phantom{RR}PH \\ \diagup \phantom{R}\| \\ R^2 \phantom{R} O \end{array} + O = C \begin{array}{c} \diagup R^3 \\ \diagdown R^4 \end{array} \xrightleftharpoons{} \begin{array}{c} R^1 \phantom{RR} R^3 \\ \diagdown \phantom{R} \diagup \\ P-C \\ \diagup \| \phantom{R} | \diagdown \\ R^2 \phantom{R} O \phantom{R} OH \phantom{R} R^4 \end{array} \quad (A)$$

(I)                                               (II)

In the above equation, $R^1$ and $R^2$ are as defined above, $R^3$ is a hydrogen atom or hydrocarbon residue having not more than about 20 carbon atoms, and $R^4$ is a hydrocarbon residue having not more than about 20 carbon atoms.

According to the investigation by the present inventors, in the hydroformylation system, a part of the secondary phosphine oxide of general formula (I) is at least partially converted into an organophosphorus compound of general formula (II) as a result of the reaction of it with the product aldehyde. And, a large part of the organophosphorus compound of general formula (II) is decomposed thermally to the secondary phosphine oxide during the distillation of the products, although the degree of decomposition of the said organophosphorus compound is strongly dependent on the kinds of $R^1$, $R^2$, $R^3$ and $R^4$. This means that the addition of an organophosphorus compound of general formula (II) to the hydroformylation system is entirely equivalent in its effect to the addition of the corresponding secondary phosphine oxide of general formula (I). Therefore, in accordance with the present invention, an organophosphorus compound of general formula (II) may be added instead of the secondary phosphine oxide of general formula (I), if so desired.

The secondary phosphine oxide of general formula (I) may be the one previously synthesized by a conventional method, or may be the one prepared in a preparation vessel provided separately and fed without isolation thereof to the hydroformylation vessel, or may be the one prepared in situ in the hydroformylation reaction system or in the step of distillation of the products. Preferred examples of the organophosphorus compound to be used in cases where the secondary phosphine oxide is not the one previously synthesized are secondary phosphines represented by the general formula (III)

wherein $R^1$ and $R^2$ are as defined above, and phosphinites represented by the general formula (IV)

wherein $R^1$ and $R^2$ are as above defined and $R^5$ is a saturated aliphatic hydrocarbon residue. The secondary phosphines of general formula (III) easily undergo oxidation by oxygen, as is known from J. Org. Chem., 26, 4626 (1961), for instance, to be converted into the corresponding secondary phosphine oxides according to the equation (B) shown below:

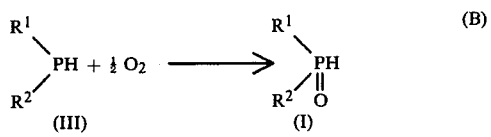

The phosphinites of general formula (IV) are easily hydrolyzed in the presence of water according to the equation (C) shown below and give the corresponding secondary phosphine oxides, as is known from G. M. Kosolapoff and L. Maier: Organic Phosphorus Compounds, vol. 4, p. 497 (John Wiley & Sons, Inc., 1972):

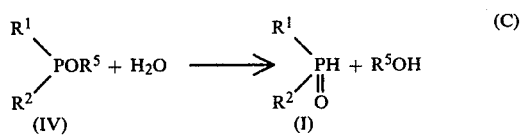

The secondary phosphine oxide of general formula (I) can, thus, be prepared in situ during the hydroformylation reaction or in the step of distillation of the products by adding to the system a secondary phosphine of general formula (III) or a phosphinite of general formula (IV), in the presence of oxygen or water.

In general formula (II), examples of $R^3$, in addition to hydrogen atom, are saturated aliphatic hydrocarbon residues such as methyl, ethyl, propyl, butyl, pentyl, hexyl, heptyl, octyl, nonyl, decyl and dodecyl, aromatic hydrocarbon residues such as phenyl, tolyl, ethylphenyl and xylyl and alicyclic hydrocarbon residues such as cyclohexyl and methylcylohexyl. Examples of $R^4$ are saturated aliphatic hydrocarbon residues such as methyl, ethyl, propyl, butyl, pentyl, hexyl, heptyl, octyl, nonyl, decyl and dodecyl, aromatic hydrocarbon residues such as phenyl, tolyl, ethylphenyl and xylyl and alicyclic hydrocarbon residues such as cyclohexyl and methylcyclohexyl.

In general formula (IV), $R^5$ is preferably a saturated aliphatic hydrocarbon residue having not more than about 20 carbon atoms, such as methyl, ethyl, propyl, butyl, pentyl, hexyl or octyl.

When a secondary phosphine oxide of general formula (I) is employed, it is necessary that it be present in the reaction system in an amount of at least one mole per gram atom of rhodium. Amounts of secondary phosphine oxide smaller than one mole are unfavorable because no substantial effect of stabilizing the rhodium catalyst is produced. Although there is no critical upper limit to the amount of said secondary phosphine oxide, it is preferable in respect of the rate of reaction and from an economic standpoint that the amount is not more than about 500 moles per gram atom of rhodium. The most preferable range of the amount in question is from 2.5 to 100 moles per gram atom of rhodium.

The same as mentioned above concerning the secondary phosphine oxide can apply to the amount of the organophosphorus compounds of general formula (II) should they be employed.

The rhodium catalyst to be used may be a rhodium carbonyl complex or any known rhodium compound which is capable of forming a rhodium complex in the reaction system. Concrete examples among a number of rhodium compounds usable as the catalysts are rhodium oxide, rhodium acetylacetonate, rhodium chloride, rhodium salts of organic carboxylic acids, $Rh_4(CO)_{12}$, $Rh_6(CO)_{16}$, $RhCl (PPh_3)_3(PPh_3$ being triphenylphosphine), $[RhCl(CO)_2]_2$, $[RhCl(COD)_2]_2$ (COD being cyclooctadiene) and $HRh(CO)(PPh_3)_3$. It is also possible to prepare the rhodium catalyst in a separate catalyst preparation vessel by a conventional method and feed the reaction mixture containing the resulting rhodium carbonyl complex to the hydroformylation vessel without any further treatment of said reaction mixture. Commercially, it is advantageous to select the concentration of the rhodium catalyst in the reaction system within the range of 0.01–10 milligram atom of rhodium (calculated as metallic rhodium) per liter of the reaction mixture.

The olefinic compounds to which the present invention is applicable include those olefins, alcohols, esters and ethers that have each a carbon-carbon double bond in the molecule. To be concrete, they are, for example, ethylene, propylene, 1-butene, 4-methyl-1-pentene, 1-hexene, 1-octene, 1-dodecene, 1,11-dodecadiene, alpha-olefins from ethylene polymerization, propylene trimer, allyl alcohol, acrolein acetal, vinyl acetate, allyl methyl ether, isobutylene, diisobutylene, isobutylene-1-butene codimer, 2-methyl-1-buten-4-ol, 2-hexene, 2-pentene, 4-methyl-2-pentene, cyclopentene, cyclohexene and cycloheptene.

The hydroformylation reaction according to the invention can be carried out in a conventional manner and under conditions generally employed, except that the reaction is carried out in the presence of the secondary phosphine oxide of general formula (I).

Any kind of organic solvents can be used in the present hydroformylation as long as it does not hamper the hydroformylation reaction. Advantageously from a commercial standpoint, the starting olefins, the product aldehydes and their condensations products can serve also as solvents for the reaction. Other preferred examples of the solvents are aromatic hydrocarbons such as benzene, toluene, xylene and dodecylbenzene, alicyclic hydrocarbons such as cyclohexane, ethers such as dibutyl ether, ethylene glycol dimethyl ether, diethylene glycol diethyl ether, triethylene glycol dimethyl ether and tetrahydrofuran, and esters such as diethyl phthalate and dioctyl phthalate. Such physical characteristics as the boiling point differences between the starting material and reaction products and the solvent are of course considered in selecting the solvent.

The reaction temperature and the temperature in the distillation still are of importance in order to stabilize the rhodium catalyst. In practicing the invention, the reaction temperature is preferably maintained at 50°–150° C. and the temperature in the distillation still at 50°–200° C. Though the thermal decomposition of the rhodium catalyst is suppressed by the method according to the invention, higher reaction temperatures than 150° C. and/or higher distillation temperatures than 200° C. may cause a decrease in the catalytic activity, partial thermal decomposition of the rhodium catalyst and/or partial degeneration of the product aldehydes.

In cases where the product aldehydes have relatively low boiling points, the major part of them can be taken out together with the off gas from the reaction system and therefore the catalyst components can be reused with ease. In those cases where the product aldehydes have relatively high boiling points, they are generally separated by distillation (under reduced pressure) and the distillation residue containing the catalyst components is recycled to the hydroformylation step.

The hydrogen/carbon monoxide partial pressure ratio to be employed in practicing the invention is preferably in the range of $\frac{1}{2}$ to 5/1 on the feed gas basis. Gases inert to the hydroformylation reaction, such as nitrogen, helium, argon, methane, ethane, propane and butanes, may be present in the reaction system.

The reaction pressure is selected depending upon the kind of the starting olefinic compound within the range of atmospheric pressure to about 300 atmospheres. As a result of the addition of the secondary phosphine oxide of general formula (I), however, the catalytic activity can be held even at pressures lower than those employed in the conventional methods.

The method of the invention can be applied preferably to those olefinic compounds that have a $CH_2=CH-$ group. In the case of these olefinic compounds, the catalyst life is stabilized and a high selectivity toward normal aldehydes is attained if the reaction is carried out in the presence of a trisubstituted phosphine in excess as compared with the amount of the rhodium catalyst. Generally, the trisubstituted phosphine is used in such an amount that its concentration in the reaction system be 10-500 millimoles per liter, preferably 25-300 millimoles per liter.

Among a large number of trisubstituted phosphines which are usable, preferred in respect of the catalytic activity, selectivity and catalyst life, etc. are trisubstituted phosphines and phosphites which are represented by the general formula

PR'R"R''' wherein R', R" and R''' are the same or different and each is aryl, aryloxy, alkyl or alkoxy, and especially preferred are triphenylphosphine, tritolylphosphine, trinaphthylphosphine, diphenyl-propylphosphine, triphenyl phosphite, trimethyl phosphite, triethyl phosphite and tributyl phosphite.

Moreover, in some cases, the activity of the catalyst for the hydroformylation of the olefinic compounds having a $CH_2=CH-$ group is stabilized to a still greater extent if 0.20–2.5 moles per gram atom of rhodium in the rhodium catalyst of a diphosphinoalkane represented by the general formula (V)

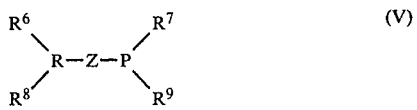

is added in combination with said secondary phosphine oxide of general formula (I) and said trisubstituted phosphine. In general formula (V), $R^6$ and $R^7$ are each aromatic hydrocarbon residues, $R^8$ and $R^9$ are each aromatic hydrocarbon residues or saturated hydrocarbon residues containing one or more carbon atoms, and Z is an alkylene radical whose main straight chain portion contains 2–5 carbon atoms and which may be substituted by one or more lower alkyl groups. In said diphosphinoalkane with such a stabilizing effect, $R^6$ and $R^7$ are each, for example, phenyl, tolyl, xylyl or naphthyl. Examples of $R^8$ and $R^9$ are such aromatic hydrocarbon residues as phenyl, tolyl and xylyl and such, saturated hydrocarbon residues as methyl, ethyl, propyl, butyl, pentyl, hexyl, heptyl, octyl and cyclohexyl. Preferred examples of the diphosphinoalkanes are as follows:

$Ph_2PCH_2CH_2PPh_2$

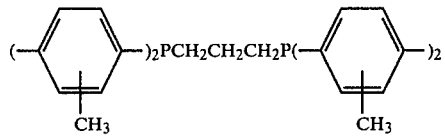

$Ph_2PCH_2CH_2CH_2CH_2PPh_2$

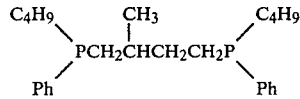

When in the case of the olefinic compounds having a $CH_2=CH-$ group) besides adding the trisubstituted phosphine and diphosphinoalkane to the reaction system, the reaction pressure is maintained at a level as low as atmospheric pressure to about 30 atmospheres, normal aldehydes are obtained with high selectivity.

In the case of the hydroformylation of olefinic compounds other than those having a $CH_2=CH-$ group in the molecule, their reactivity is low as compared with the olefinic compounds having a $CH_2=CH-$ group. Therefore higher reaction pressures (e.g. about 100 atmospheres) are required to obtain such reaction rates as would be satisfactory from a commercial standpoint. It is not always necessary to add the trisubstituted phosphine to the reaction system when hydroformylating a compound without a $CH_2=CH-$ group because the observed effect of adding the tri-substituted phosphine is not as great as in the case of the olefinic compounds having a $CH_2=CH-$ group in their molecule due to influences of the skeletal structure of the starting olefinic compounds.

The following examples will illustrate the present invention in more detail. In the Examples and Examples for Comparison, each hydroformylation reaction was carried out in a one-liter stainless steel autoclave equipped with thermometer, magnetic stirrer, gas inlet, reflux condenser, opening valves for sampling and gas outlet. In Example 5 and the subsequent examples, the autoclave was connected to an external gas reservoir which was filled with a gas having the same composition as that of the gas in the autoclave via a pressure adjusting valve so that the gas portion consumed by the rection might be supplemented and the pressure in the autoclave might be kept at a constant level during the reaction.

EXAMPLE 1

The autoclave was charged with a mixed solution consisting of 250 ml of a dioctyl phthalate solution containing 0.40 millimole of $HRh(CO)(PPh_3)_3$, 20 millimoles of $PPh_3$ and 4.0 millimoles of

and 25 ml of nonylaldehyde and with 0.80 mole of 1-octene. The autoclave was purged thoroughly with a mixed $H_2/CO$ gas ($H_2/CO=3/1$ in molar ratio) and then heated to a constant temperature of 90° C. (temperature within the autoclave). Thereafter, a mixed $H_2/CO$ gas (3/1 in molar ratio) was introduced into the autoclave and the contents of the autoclave were stirred while maintaining the pressure within the autoclave at 4.0 kg/cm² (absolute pressure by means of said mixed gas) and the rate of flow of the effluent gas at 20 Nl/hr (hereinafter the time when said stirring was begun is called the time of commencement of the reaction). After 1.5 hours the stirring was discontinued, the autoclave was allowed to cool and depressurized, and the reaction mixture was analyzed by gas chromatography. It was revealed that the remaining unreacted 1-octene amounted to 0.016 mole and the yield of normal-and iso-nonylaldehydes (hereinafter called nonylaldehydes) was 0.729 mole in total.

Then the unreacted starting material and the products were distilled off over about an hour in a hydrogen atmosphere while maintaining the autoclave temperature at 130°–140° C. and varying the degree of reduction in pressure depending upon the rate of flow of the distillate. Gas chromatographic analysis of the residue showed that there was no 1-octene remaining in the residue but there was 0.040 mole of nonylaldehydes remaining therein.

Into the dioctyl phthalate solution (distillation residue) containing the catalyst components, there was introduced 0.80 mole of fresh 1-octene under pressure, and the hydroformylation reaction was carried out for 1.5 hours by the procedure of the first run. Analysis of the reaction mixture by gas chromatography revealed that the yield of nonylaldehydes in the second run was 0.728 mole and the amount of the unreacted 1-octene was 0.017 mole.

The reaction mixture was subjected to reduced pressure distillation by the procedure of the first run, and the residue analyzed. The autoclave was then charged again with 0.80 mole of 1-octene and the hydroformylation was carried out for 1.5 hours by the procedure of the first run. Analysis of the reaction mixture showed that the yield of nonylaldehydes in this third run was 0.721 mole and the amount of the remaining unreacted 1-octene was 0.025 mole.

It can be seen from the above that the catalytic activity did not decrease substantially in the repeated three runs. In said three runs, each reaction mixture had a yellow color.

EXAMPLE FOR COMPARISON 1

Two consecutive runs of the hydroformylation of 1-octene were carried out by the procedure and under the conditions of Example 1 except that no

was added. The nonylaldehydes yields in the first and the second runs were 0.730 and 0.370 mole, respectively, and the amounts of the unreacted 1-octene in the first and the second runs 0.015 and 0.381 mole, respectively.

Thus, without the addition of

the catalytic activity decreased remarkably. The reaction mixture had a dark brown color.

EXAMPLE 2

The autoclave was charged with a mixed solution consisting of 150 ml of n-butyraldehyde and a solution of 0.40 millimole of $HRh(CO)(PPh_3)_3$, 30 millimoles of $PPh_3$, 16 millimoles of

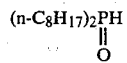

and 0.20 millimole of $Ph_2P(CH_2)_2PPh_2$ in 250 ml of dioctyl phthalate, the system was purged thoroughly by means of a mixed $H_2/CO$ gas (2/1 in molar ratio), and then the contents were heated to and maintained at 100° C., while introducing propylene, carbon monoxide, hydrogen and nitrogen through the gas inlet at the rates of flow of 50, 30, 60 and 70 liters per hour, respectively, the pressure within the autoclave was maintained at 17.0 kg/cm² (absolute pressure). The reslting butyraldehydes (normal- and iso-butyraldehydes) were taken out continuously together with the effluent gas. It was confirmed by the use of a level meter fitted to the autoclave that the amount of the liquid phase in the reactor, after reaching a stationary state, always remained constant. The product butyraldehydes were collected by bubbling the effluent gas in a toluene trap cooled in an acetone-dry ice bath at specified intervals, and gas chromatographed for their contents. The rates of formation of butyraldehydes at 20 hours and 200 hours after the commencement of the reaction thus determined were 1.022 and 1.001 moles per hour, respectively.

EXAMPLE FOR COMPARISON 2

The hydroformylation of propylene was carried out by the procedure and under the conditions of Example 2 except that no

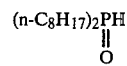

and no $Ph_2P(CH_2)_2PPh_2$ were added. The rates of formation of butyraldehydes at 20 hours and 200 hours after the commencement of the reaction were 1.036 moles per hour and 0.642 mole per hour, respectively.

EXAMPLE 3

The autoclave was charged with 350 ml of a toluene solution containing 0.40 millimole of $HRh(CO)(PPh_3)_3$, 20 millimoles of $PPh_3$, 2.0 millimoles of

and 0.10 millimole of $Ph_2P(CH_2)_4PPh_2$ and with 0.40 mole of allyl alcohol. The autoclave was purged thoroughly by means of a mixed $H_2/CO$ gas (3/1 in molar ratio), and the contents were then heated to a constant temperature of 75° C. Then a mixed $H_2/CO$ gas (3/1 in molar ratio) was introduced into the autoclave, and stirring was begun while maintaining the pressure at 3.0 kg/cm² (absolute pressure) and the rate of flow of the effluent gas at 10 Nl/hr. The whole amount of the effluent gas was introduced into a toluene trap in a acetone-dry ice bath so that the accompanying allyl alcohol, propanal and other low-boiling products might be collected in said trap. The hydroformylation of allyl alcohol was continued in this manner for 2 hours. Gas chromatographic analysis of the reaction mixture showed that 0.016 mole of the allyl alcohol remained unreacted.

The autoclave was then charged with an additional 0.40 mole of allyl alcohol, and the hydroformylation reaction was conducted for an hour by the same procedure. Analysis by gas chromatography revealed that the reaction mixture contained 0.020 mole of unreacted allyl alcohol. Thereafter, two additional runs of the hydroformylation were carried out by adding each 0.40 mole of allyl alcohol at hourly intervals and following the same procedure as above. The unreacted allyl alcohol contents in the reaction mixtures after respective hourly periods of reaction were 0.022 and 0.026 mole, respectively.

EXAMPLE FOR COMPARISON 3

Four repeated runs of the hydroformylation of allyl alcohol were conducted by the procedure and under the conditions of Example 3 except that the addition of

and the addition of $Ph_2P(CH_2)_4PPh_2$ were omitted. The unreacted allyl alcohol in the first, second, third and fourth runs amounted to 0.008, 0.032, 0.065 and 0.096 mole, respectively.

EXAMPLE 4 AND EXAMPLE FOR COMPARISON 4

The autoclave was charged with 275 ml of a dodecylbenzene solution containing 0.40 millimole of HRh(CO)(PPh₃)₃, 25 millimoles of P

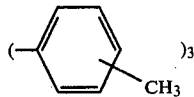

and 6.0 millimoles of (n-C₈H₁₇)₂P(=O)CH(OH)C₆H₁₃ and with 1.0 mole of 1-hexene, and, while introducing a mixed H₂/CO gas (3/1 in molar ratio) at such a rate that the rate of flow of the effluent gas might be kept at 20 Nl/hr, the reaction was carried out for 1.5 hours under the condition of 5.0 kg/cm² (absolute pressure) and 90° C. (temperature of the contents).

The reaction mixture was subjected to reduced pressure distillation by the procedure of Example 1 while maintaining the temperature within the autoclave at 120°–130° C.

Five runs in total of the hydroformylation of 1-hexene were repeated by the above procedure with 1.0 mole of 1-hexene being fed in each run. The yields of heptanals in the first and the fifth runs were 0.897 and 0.879 mole, respectively, and the amounts of unreacted 1-hexene in said runs were 0.030 and 0.039 mole, respectively.

When the hydroformylation of 1-hexene followed by the distillation was repeated under the same conditions as in Example 4 except that the addition of (n-C₈H₁₇)₂P(=O)CH(OH)C₆H₁₃ was omitted, the yield of heptanals in the third run amounted only to 0.581 mole while the remaining 1-hexene amounted to 0.358 mole.

It can thus be seen that, in case where (n—C₈H₁₇)₂P(=O)CH(OH) C₆H₁₃ is used, too, the catalytic activity does not show any substantial decrease.

EXAMPLE 5

The autoclave was charged with 250 ml of a dodecylbenezene solution containing 0.10 millimole of [RhCl(CO)₂]₂ and 2.5 millimoles of Ph₂PH
O and with 170 g (1.515 moles) of diisobutylene (content of terminal double bond-containing olefin =87%). The autoclave was then purged thoroughly with a mixed H₂/CO gas (1/1 in molar ratio), and thereafter, the reaction was conducted for 4 hours under a pressure of a mixed H₂/CO gas (1/1 in molar ratio) of 120 kg/cm² (absolute pressure) and at 125° C. with vigorous stirring. A very small amount of the reaction mixture was taken as a sample and analyzed by gas chromatography. The conversion of diisobutylene was 85% and the yield of isononylaldehyde was 1.279 moles.

The unreacted starting material and the reaction products were then distilled off over about an hour while maintaining the temperature within the autoclave at 130°–140° C. and altering the degree of reduction in pressure depending upon the rate of distilling off as in Example 1. Into the catalyst-containing dodecylbenzene solution remaining after the distillation there was introduced another 170 g of diisobutylene, and the reaction was conducted for 4 hours under the same conditions as above. Analysis of the reaction mixture showed that the yield of isononylaldehyde was 1.259 moles. By repeating the same procedure (170 g of diisobutylene being fed in each run), five runs in all were conducted. The yield of isononylaldehyde in the fifth run was 1.220 moles. The reaction mixture in the fifth run was apparently a homogeneous yellow solution.

EXAMPLE FOR COMPARISON 5

Two runs of the hydroformylation of diisobutylene were conducted by the procedure and under the conditions of Example 5 except that the addition of Ph₂PH
O was omitted. The yields of isononylaldehyde in the first and the second runs were 1.290 moles and 0.864 mole, respectively. In this manner, without the addition of Ph₂PH,
O of only two repetitions of the reaction cause significant decrease in the catalytic activity. The reaction mixture in the second run apparently had a dark brown color.

EXAMPLE 6

The autoclave was charged with 350 ml of a dioctyl phthalate solution containing 4.0 mg (0.00054 mml) of Rh₄(CO)₁₂ and 0.173 g (0.856 mml) of Ph₂PH
O and with 130 g (1.512 moles) of 2-methyl-1-buten-4ol. After thoroughly purging the autoclave with a mixed H₂/CO gas (1/1 in molar ratio), the reaction was carried out at a pressure of 140 kg/cm² (absolute pressure) resulting from a mixed H₂/CO gas (1/1 in molar ratio) and at a temperature of 100° C., with stirring, for 4 hours. After the reaction, a very small amount of the reaction mixture was taken out and analyzed by gas chromatography, to show that 0.045 mole of the 2-methyl-1-buten-4-ol remained unreacted (the conversion being 97%), that the yield of 2-hydroxy-4-methyl-tetrahydropyran was 1.320 moles, and that the yields of 2-methyl-2-buten-4-ol and isovaleraldehyde were 0.058 and 0.073 mole, respectively.

The unreacted starting material and the products were distilled off over about an hour while maintaining the temperature within the autoclave at 120°–130° C. and altering the degree of reduction in pressure depending upon the rate of distilling off as in Example 1.

Into the catalyst-containing dioctyl phthalate solution remaining after the distillation, there was introduced again 130 g of 2-methyl-1-buten-4ol under pressure and the reaction was repeated under the same conditions as above for 4 hours. Analysis of the reaction mixture gave the yield of 2-hydroxy-4-methyl-tetrahydropyran of 1.303 moles. By repeating the same procedure (130 g of 2-methyl-1-buten-4-ol being fed in each run), five runs in total were conducted. The yield of 2-hydroxy-4-methyltetrahydropyran in the fifth run was 1.238 moles. The reaction mixture in the fifth run was apparently a homogeneous pale-yellow liquid.

EXAMPLE FOR COMPARISON 6

Two runs of the hydroformylation of 2-methyl-1-buten-4-ol were conducted by the procedure and under the conditions of Example 6 except that the addition of

was omitted. The yields of 2-hydroxy-4-methyltetrahydropyran in the first and the second runs were 1.323 moles and 0.820 mole, respectively. In this manner, without the addition of

only two repetitions of the reaction bring about significant decrease in the catalytic activity.

What is claimed is:

1. A process for hydroformylating an olefinic compound to obtain an aldehyde having an additional carbon atom, which process comprises contacting said olefinic compound with carbon monoxide and hydrogen in the presence of a rhodium catalyst and in the presence of an added secondary phosphine oxide having the formula (I) in an

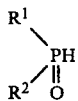

amount of at least one mole per gram atom of rhodium, wherein $R^1$ and $R^2$ are the same or different and each is a substituted or unsubstituted hydrocarbon residue containing not more than about 20 carbon atoms.

2. A process as claimed in claim 1, wherein the residues $R^1$ and $R^2$ in the secondary phosphine oxide of formula (I) are each selected from the group consisting of saturated aliphatic hydrocarbon residues, aromatic hydrocarbon residues and alicyclic hydrocarbon residues, with and without one or more substituents selected in turn from the group consisting of heteroatoms and heteroatom-containing groups comprising the fluorine atom, lower alkoxy, hydroxyl and amino.

3. A process as claimed in claim 1, wherein said secondary phosphine oxide of formula (I) is added in an amount of 1-500 moles per gram atom of rhodium.

4. A process as claimed in claim 3, wherein said secondary phosphine oxide is added in an amount of 2.5-100 moles per gram atom of rhodium.

5. A process as claimed in claim 1, wherein an organophosphorus compound having the formula (II)

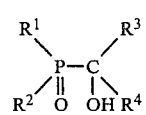

is added as a presursor of said secondary phosphine oxide of formula (I) in an amount of 1-500 moles per gram atom of rhodium, wherein, in formula (II), $R^1$ and $R^2$ are the same or different and each is a substituted or an unsubstituted hydrocarbon residue containing not more than about 20 carbon atoms, $R^3$ is a hydrogen atom or a hydrocarbon residue containing not more than about 20 carbon atoms and $R^4$ is a hydrocarbon residue containing not more than about 20 carbon atoms.

6. A process as claimed in claim 5, wherein said organophosphorus compound of formula (II) is added in an amount of 2.5-100 moles per gram atom of rhodium.

7. A process as claimed in claim 1, wherein said olefinic compound has a $CH_2=CH-$ group.

8. A process as claimed in claim 7, wherein a trisubstituted phosphine is added to the reaction system in combination with said secondary phosphine oxide of formula (I) to a concentration of said trisubstituted phosphine in the reaction system of 10-500 millimoles per liter.

9. A process as claimed in claim 8, wherein a diphosphinoalkane having the formula (V)

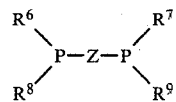

is added to the reaction system in combination with said secondary phosphine oxide and with said trisubstituted phosphine, in an amount of 0.20-2.5 moles per gram atom of rhodium, wherein, in formula (V), $R^6$ and $R^7$ are each aromatic hydrocarbon residues, $R^8$ and $R^9$ are each aromatic hydrocarbon residues or saturated hydrocarbon residues containing one or more carbon atoms and Z is an alkylene radical whose main straight chain contains 2-5 carbon atoms and which may be substituted with one or more lower alkyl groups.

10. A process as claimed in claim 7, wherein the reaction pressure is in the range of atmospheric pressure to about 30 atmospheres.

11. A process as claimed in claim 1, wherein the concentration of said rhodium catalyst as calculated as metallic rhodium is in the range of 0.01-10 milligram atom per liter.

12. A process as claimed in claim 1, wherein the reaction temperature is 50°-150° C.

13. A process as claimed in claim 1, wherein the partial pressure ratio of hydrogen to carbon monoxide is in the range of ½ to 5/1 on the feed gas basis.

14. A process as claimed in claim 1, wherein the reaction pressure is in the range of atmospheric pressure to about 300 atmospheres.

15. A process as claimed in claim 1, wherein there is obtained a reaction mixture comprising the aldehyde reaction product and unreacted starting material containing the catalyst; the reaction mixture is separated by distillation; and the catalyst-containing material is reused by recycling it directly to the reaction site.

* * * * *